Figure 1:
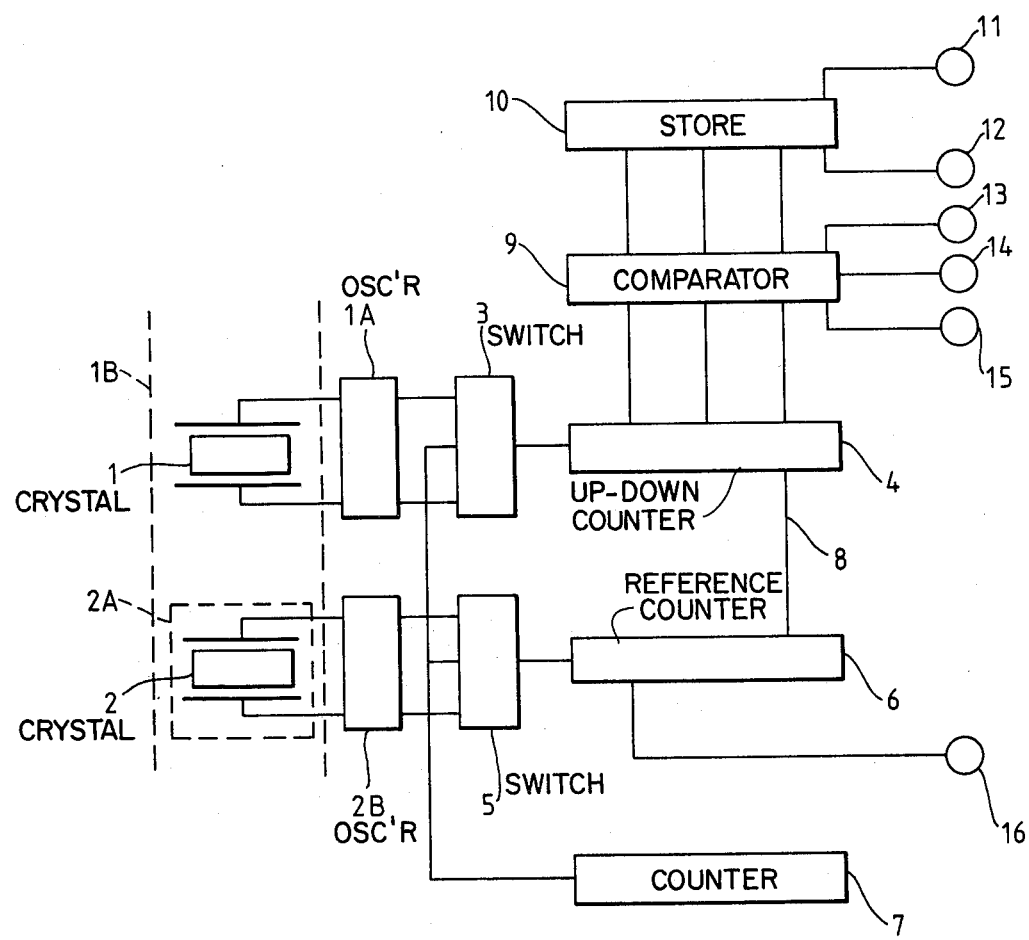

United States Patent [19]

Sinclair

[11] 4,446,720

[45] May 8, 1984

[54] METHOD AND APPARATUS FOR DETECTING THE PRESENCE OF A CONTAMINANT IN A GASEOUS CARRIER

[75] Inventor: Ian Sinclair, Loughborough, England

[73] Assignee: The Secretary of State for Social Services in Her Britannic Majesty's Government of the United Kingdom of Great Britain and Northern Ireland, London, England

[21] Appl. No.: 328,589

[22] PCT Filed: Apr. 10, 1981

[86] PCT No.: PCT/GB81/00064

§ 371 Date: Nov. 25, 1981

§ 102(e) Date: Nov. 25, 1981

[87] PCT Pub. No.: WO81/03071

PCT Pub. Date: Oct. 29, 1981

[30] Foreign Application Priority Data

Apr. 18, 1980 [GB] United Kingdom ................. 8012889

[51] Int. Cl.³ ........................................... G01N 27/00
[52] U.S. Cl. ...................................................... 73/23
[58] Field of Search ............... 73/23, 28, 29; 340/602, 340/627, 632

[56] References Cited

U.S. PATENT DOCUMENTS

| | | | |
|---|---|---|---|
| 3,561,253 | 2/1971 | Dorman | 73/28 |
| 3,595,069 | 7/1971 | Fowler | 73/579 |
| 3,689,907 | 9/1972 | Guajardo | 340/602 |
| 3,715,911 | 2/1973 | Chuan | 73/28 |

FOREIGN PATENT DOCUMENTS

| | | | |
|---|---|---|---|
| 986011 | 3/1965 | United Kingdom. | |
| 1017188 | 1/1966 | United Kingdom. | |
| 1049742 | 11/1966 | United Kingdom. | |
| 1063589 | 3/1967 | United Kingdom. | |
| 1065558 | 4/1967 | United Kingdom. | |
| 1086907 | 10/1967 | United Kingdom. | |
| 1314305 | 4/1973 | United Kingdom | 73/23 |

*Primary Examiner*—Stephen A. Kreitman
*Attorney, Agent, or Firm*—Stevens, Davis, Miller & Mosher

[57] ABSTRACT

The invention concerns the detection of contaminant in a stream of gas. Previous methods have either been insufficiently sensitive or have been slow and needed skilled operatives. The present invention allows speedy operation with relatively unskilled operatives. A piezo electrical crystal oscillator (1) is allowed to oscillate for a known period of time and the number of oscillations is counted. For a known time the crystal is exposed to contaminant, and is then allowed to oscillate again for the same period of time as before and the oscillations again counted. The difference in number of oscillations is a measure of the mass of contaminant deposited on the crystal (1). The period of oscillation of the first crystal is determined by a second matched crystal oscillator (2) in which the crystal is exposed to the same environment but not in contaminant. The apparatus has the advantage of being self-zeroing, and the exposed crystal (1) does not need cleaning after each use. The invention has special application to the testing of medical gases, for example oxygen and nitrous oxide.

13 Claims, 2 Drawing Figures

METHOD AND APPARATUS FOR DETECTING THE PRESENCE OF A CONTAMINANT IN A GASEOUS CARRIER

This invention relates to a method and apparatus for detecting the presence of contaminants in a gaseous carrier and has particular but not exclusive reference to the detection of minute quantities of particulate material in a gaseous carrier.

It is known that the presence of very small quantities of particulate material in a gaseous carrier can be detected by impacting the particles on to the surface of a piezo-electric crystal forming part of an electrical oscillator. The resultant increase in mass of the crystal reduces the frequency of oscillation and thereby provides an indication of the presence of particulate material in the carrier and, if required, a measurement of the mass of such material deposited on the crystal.

By suitable treatment of the surface of the crystal, for example by coating the surface with an appropriate substrate, the presence of gaseous contaminants may be detected, such contaminants interacting with the substrate to cause an increase or decrease in the mass of the crystal and hence a decrease or increase in the frequency of oscillation.

Examples of apparatus embodying the techniques just described are to be found in U.S. Pat. No. 3,561,253. That Specification describes various methods of impacting contaminants on to the surface of a piezo-electric crystal forming part of an electric oscillator including the use of jet orifices to impact particulate material on to that surface. A reduction in the frequency of oscillation of the crystal is indicated either by means of a counter fed directly by the oscillator or by beating the output of the oscillator which that of a standard oscillator with a piezo-electric crystal exposed to the same environmental conditions as the first mentioned crystal but not exposed to the impaction of particulate material or other contaminant being detected and/or measured. The beats are counted by a counter to indicate frequency changes.

The use of two crystals has the advantage that the effect of frequency shifts caused by changes in environmental factors, for example temperature, are eliminated.

However, such apparatus is normally operated by skilled personnel who are able to evaluate the counter readings. In addition, it is necessary to clean the surface of the crystal thoroughly between successive measurements and this is a time-consuming and laborious task.

The present invention provides a method and apparatus which allows the aforementioned disadvantages to be substantially avoided.

According to the invention apparatus for detecting the presence of a contaminant in a gaseous carrier comprises a first piezo electric crystal oscillator, carrier gas feed means for enabling contaminant to act upon the said first crystal in a manner which changes the effective mass thereof, measuring means for obtaining a first value related to the total number of oscillations of the crystal during a predetermined period of time, and an arrangement for enabling the first value to be decreased by a second value related to the total number of oscillations of the crystal during a second time period not greater than said predetermined time period.

Preferably the means for producing said values are counters each arranged to produce said values as respective numerical counts.

Desirably the apparatus includes a comparator to compare the numerical count at the end of said second period with a numerical count of preset value for providing an indication as to whether the numerical count at the end of said second period is greater than or less than the preset numerical count.

The apparatus preferably includes a second piezo electric crystal oscillator the output of which drives a counter to determine the said predetermined period of time and said second period of time, the second piezo electric crystal being preferably exposed to substantially the same environmental conditions affecting its stability as said first crystal, except that shielding means are provided so that the second crystal is not exposed to contaminant and the mass of said second crystal remains unchanged.

Testing means are desirably provided, arranged to allow the first crystal to oscillate for a preselected period of time, to obtain a value related to the number of oscillations of the first crystal in said preselected period of time, and to compare said value with at least one other preselected value, whereby any change in mass of said crystal due to previous use can be determined.

Preferably the apparatus includes time delay means arranged to allow each piezo electric crystal oscillator to oscillate for an initial period of time and then to switch said oscillator to a respective measuring means.

In one embodiment, at least the first piezo electric crystal is provided on its surface with a substrate with which contaminant in a gaseous carrier can interact.

Also according to the invention a method of detecting the presence of a contaminant in a gaseous carrier comprises the steps of allowing a first body i.e. a piezo electric crystal to oscillate for a predetermined period of time, obtaining a first value proportional to the total number of oscillations by the crystal during that period of time, allowing contaminant to act upon the crystal in a manner such that the mass of the crystal is changed, allowing the said crystal so acted upon to oscillate for a second time period not greater than the said predetermined time period, and decreasing said first value by a second value proportional to the total number of oscillations by the crystal during said second period.

The contaminant may act upon the surface of the said crystal to increase the mass thereof. Alternatively the contaminant may interact with a substrate on the surface of the said crystal to change the mass thereof. The above mentioned values are preferably numerical counts.

Preferably the method includes a step by which the numerical count at the end of said second period is compared with a preset value to obtain an indication of whether the change in the mass of the said crystal is above or below a particular value represented by the preset value.

The method preferably also includes defining the predetermined period of time as that required for a second piezo electric crystal to effect a predetermined number of oscillations.

Desirably the method includes the step of exposing the second crystal to substantially the same environmental conditions affecting its stability as the said first crystal, except that the second crystal is not exposed to contaminant and the mass of the second crystal remains unchanged.

The method preferably includes, before allowing contaminant to act upon the first crystal, the steps of allowing said first crystal to oscillate for a predetermined period, and of determining any change in mass of said first crystal which may be due to previous use. Desirably a numerical count is obtained which is related to the change in mass of the crystal due to said previous use, and said numerical count is compared with at least one predetermined numerical count so as to ascertain the extent of the change.

In this specification the term "contaminant" is to be understood to mean not only an undesirable substance carried by a stream of gas under investigation, but any substance the concentration of which in the carrier gas it is required to assess.

Figure 2:
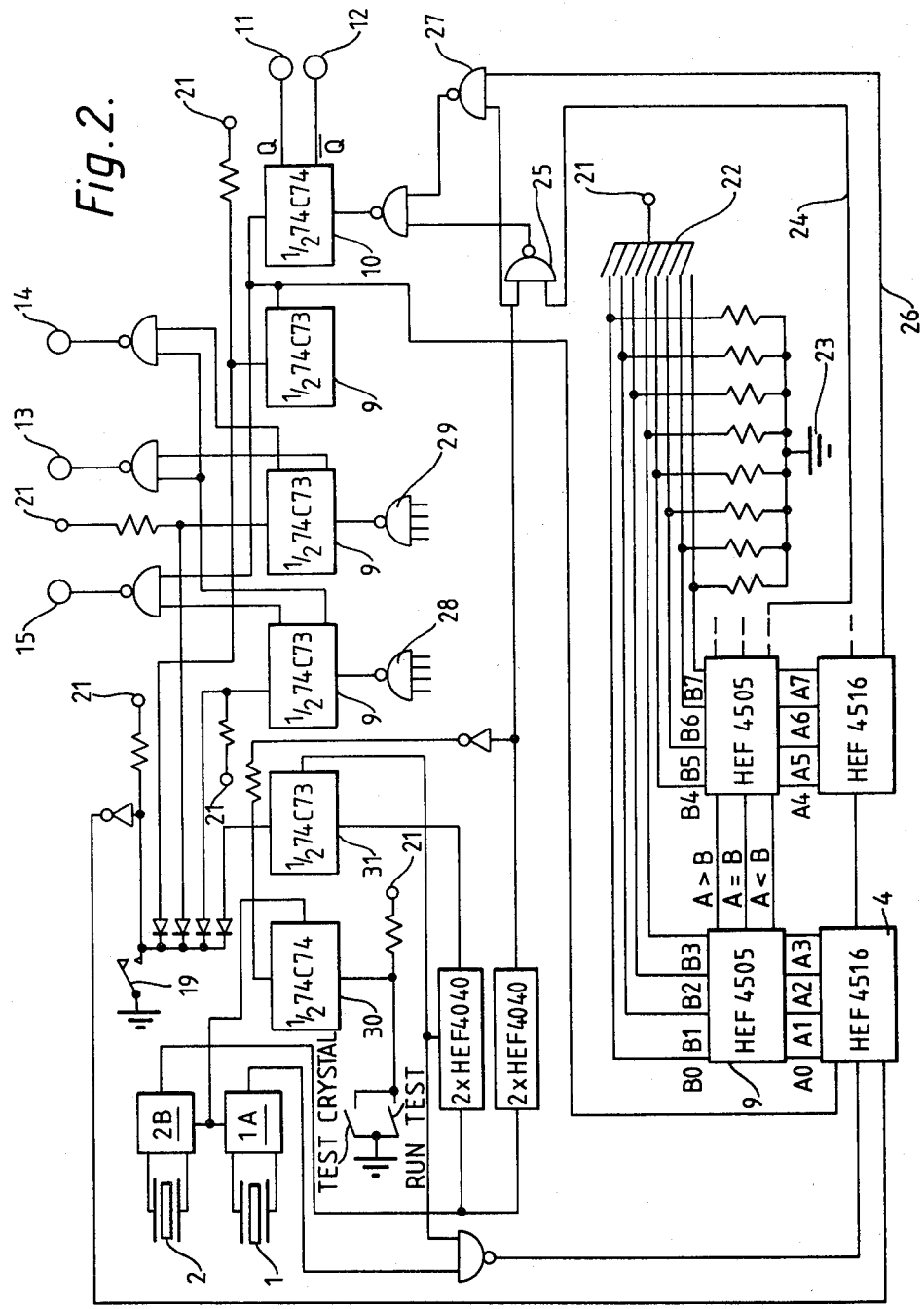

The invention will be further described, by way of example only, with reference to the accompanying drawings, in which FIG. 1 is a block schematic diagram and FIG. 2 is a more detailed illustration of the electrical circuits of the apparatus, still partly in block form.

A first piezo electric crystal 1 is connected in an electrical oscillatory circuit, which may be of conventional kind, indicated by the block 1A. The crystal is an AT cut quartz crystal with electrodes adapted to vibrate the crystal in a thickness shear mode at a frequency of 5 MHz.

The crystal is mounted in carrier gas feed means, viz a chamber 1B having an inlet comprising five impact nozzles or jets similar to that described in U.S. Pat. No. 3,561,253 and each of 1 mm diameter for impacting any particles entrained in a gaseous carrier fed to the chamber via the inlet on to the surface of the crystal 1. The nozzles are so orientated with respect to the crystal surface as to direct streams of the carrier towards the surface in a direction normal thereto. The nozzles are spaced 0.5 mm from the surface of the crystal.

The chamber has an outlet through which the carrier leaves the chamber. The outlet is so formed that the flow rate of carrier is substantially independent of initial pressure over a wide range of pressures up to say 3 MN/m². Also contained in the chamber is a second piezo electric crystal 2 housed in a conventional container 2A which protects it from contaminant and so located that it does not affect the flow of carrier on to the surface of the first crystal or from the chamber but is subject to the same conditions of temperature, pressure, humidity and the like as the first crystal. The second crystal is identical with the first and also forms part of a second similar oscillatory circuit indicated by the block 2B.

During use of the apparatus, any particulate material present in the gaseous carrier is impacted on to the surface of crystal 1 thereby increasing the effective mass thereof and decreasing the frequency of oscillation. The decrease in frequency is detected by a digital counting technique now to be described.

The output of the oscillatory circuit containing crystal 1 is applied via switching means 3 to an up-down counter 4, i.e. the measuring counter.

In a similar manner, the output of the oscillatory circuit containing crystal 2 is applied via switching means 5 to a reference counter 6.

The switching means 3 and 5 are controlled by another counter 7 in a manner to be described below.

Counters 4 and 6 are, in the example being described, able to effect counts of value $2^{22}$ and $2^{21}$ respectively.

A control connection 8 from counter 6 to counter 4 effects a change from count-up to count-down in the operation of counter 4. A conventional comparator 9 is connected both to counter 4 and to a preset count store 10.

To carry out a test to detect the presence of particulate material in a gaseous carrier, a valve controlling the admission of the carrier to the chamber 1B is first closed. The apparatus is then energised and at this stage both oscillatory circuits 1A and 2B are brought into operation as is a time delay means, in this example a counter 7. The counter 7 is preset to run for an initial period of time, (two seconds, say) long enough to allow the oscillators to settle down to a stable mode of oscillation, after which counter 7 actuates the switching means 3, 5 in such manner as to allow the output of both oscillatory circuits to be applied to their respective counters 4, 6 for a predetermined period set by the time required for counter 6 to reach its maximum counter of value $2^{21}$, counter 4 being initially in the count-up mode. When that value is reached, the condition of measuring counter 4 is changed via control connection 8 from a count-up mode to a count-down mode but the count reached in counter 4 is retained. Reference counter 6 resets.

Gaseous carrier is then admitted to the chamber via the jets in the chamber 1B and allowed to flow for a predetermined period of, say, one minute. At the end of that period, the output of the oscillator 1A containing crystal 1 is connected so as to drive counter 4 down towards zero and at the same time counter 6 is restarted.

When after the second time period counter 6 reaches a count of value $2^{21}$, counter 4 is again stopped via control connection 8.

The decreased count remaining in counter 4 will then indicate the change in frequency of oscillation of crystal 1 due to an increase in effective mass of the crystal. If the count is zero there has been no decrease in frequency, and hence no increase in mass, indicating the absence of particulate material in the gaseous carrier, or that the particulate content is insufficient to produce a detectable increase in the mass of the crystal.

If there has been an increase in the effective mass of the crystal 1, the mass can be calculated from the remaining count in counter 4. A change in frequency of 1 c/s represents an increase in mass of about $0.003\mu$ grams. Typically a crystal is about 15 mm in diameter, carrier gas impinging on it normal to a circular face thereof.

To simplify use of the apparatus in circumstances where it is required merely to know whether the quantity of particulate material in the gaseous carrier is above or below a particular value, the count remaining in counter 4 is compared in the comparator 9 with a preset count value stored in the store 10. If the count remaining in counter 4 is below the preset count value, a green light 11 is energised whereas if the count remaining in counter 4 is above the preset value a red light 12 is energised.

Preferably, such apparatus also includes a test procedure and indication which enables a user to check the condition of crystal 1 before starting a test.

In one particular embodiment, the layout of controls and indicators is such that a user by operating the controls in sequence, is provided with visual signals at the appropriate stages in the sequence by indicator lights positioned closely adjacent the relevant control.

The control panel has four control buttons or switches arranged in a horizontal line across the panel. On the left of the line is a power ON/OFF control; to its right is a "Set Zero" control 19 for bringing the counters to zero, and this is followed by a "Crystal Test" control. The final control is a "Run Test" control.

Directly above the "Crystal Test" control is a vertical line of three warning lights. The uppermost light is a green light 15, the next is an amber light 14 and the lower-most is a red light 13.

Directly above the "Run Test" control are two further lights, an upper green light 11 and a lower red light 12.

Operation of the "Crystal Test" control allows both crystals 1 and 2 to oscillate and, after a period determined by counter 7 to drive counters 4 and 6 respectively. Crystal oscillation continues for a period determined by the capacity of counter 6 and at the end of that period counter 4 is stopped and counter 6 resets to zero. The count in counter 4 is then compared with two preselected different counts stored in store 10. If the count in counter 4 is below either value, this indicates that the mass of the crystal has changed by an amount sufficient to cause a departure from the linear part of the mass/frequency relation of the crystal and it should not be used. This is indicated by the energisation of the red light 13. The departure from linearity which can be tolerated, for example, in a crystal oscillating when uncontaminated at 5 $MH_z$, can be represented by a change in resonant frequency of the order of 2 $KH_z$, i.e. a change of about 0.04 percent. In addition, an interlock of conventional kind is energised which prevents use of the apparatus beyond the "crystal test" operation.

If the count in counter 4 lies between the two values the amber light 14 is energised indicating that the mass of the crystal is approaching but has not reached the critical value at which the departure from linearity occurs, and can be used in at least one further test.

If the count in counter 4 is above the higher count, the green light 15 is energised and this indicates that the crystal is of a mass sufficiently below the critical value to allow continuing use.

Energisation of either the amber or the green light enables the test to continue to "run test". The user first admits the gaseous carrier to the chamber for a predetermined period for example one minute, by opening a flow control valve in a supply line leading to the chamber. At the end of that period, the valve is closed to terminate the supply of carrier to the chamber and the user then actuates the "Run Test" control.

That actuation enables crystal 2 for stepping counter 6 up and crystal 1 for stepping counter 4 down. When counter 6 reaches its maximum count of $2^{21}$, it actuates counter 4 via control connection 8 and the operation then proceeds as described above and one or other of the lights 11, 12 is energised to indicate a "pass" or a "fail".

Assuming that the red light 13 has not been energised during the "Test Crystal" phase, the apparatus can be re-used without the need to clean the surface of the crystal 1. The mass of particulate material already accumulated on the surface of the crystal 1 does not affect the accuracy of a subsequent reading. The apparatus is, in effect, "self-zeroing", the measuring counter 4 always starts from zero irrespective of the mass of material already accumulated on the surface of the crystal 1.

If the red light 12 is energised, the user is warned that the crystal 1 must be replaced by a "clean" crystal and the "dirty" crystal cleaned to remove the accumulated mass of particulate material. Better than twenty tests should be available from a crystal before cleaning is required, if all tests are conducted on carrier gas having just insufficient contaminant to be detected by less sensitive means. In the case of carrier gases, for example medical gases, which normally have a very low degree of contamination, it may be found that up to hundreds of tests can be made before crystal cleaning becomes necessary.

Other safety and/or warning devices may be fitted to the apparatus. For example, if, after the expiration of the time delay set by counter 7, the reference counter 6 operates correctly, a flashing light 16 indicates that the test may proceed. Absence of flash indicates that the counter 6 has failed to operate correctly and that a fault condition exists.

The presence of the second crystal 2 and its associated oscillatory circuit 2B operating counter 6, ensures that temperature, humidity, pressure and the like changes in the chamber 1B do not affect the accuracy of the measurements.

The invention has been described principally in relation to the detection of particulate contamination in a gas flow. By suitable treatment of the crystal surface the presence of gaseous contaminants may also be detected and/or measured using the techniques described above with reference to the drawing.

In some cases, a substrate on the crystal may be used which loses mass on interaction with contaminant in a gaseous carrier. For example, the substrate may contain absorbed water some or all of which may be released to a dry gaseous carrier and thereby provide an indication of the degree of dryness of the carrier. In this case, counter 4 may be driven up to a number X during the predetermined time period and then during the "Run Test" is allowed to run down for a time period equal to one half of the predetermined time value. Any decrease in the mass of the crystal will show as a count in counter 4 of a value below X/2—the difference indicating the extent of the decrease.

It will be appreciated that the apparatus described with reference to the drawing provides an immediate indication of the level of particulate contaminant which can be interpreted by relatively unskilled operatives and that the crystal can be operated in a "dirty" condition provided that in such condition the effective mass of the crystal does not approach the critical value referred to above, at which departure from linearity of the mass/-frequency relation of the crystal becomes unacceptable.

As has been described above, the measuring counter 4 is made to count up to a value and then count down again through a number of counts which in general is less than the number through which it counted up. In testing very clean carrier gas supplies, it may be that during the "Run Test" operation no measurable amount of contaminant is deposited on the crystal 1. In these circumstances ideally the counter 4 having commenced at zero should finish at zero. However, owing to inevitable slight inprecision of operation in counters it could happen that the count down continues beyond zero. The counter is not constructed to indicate a negative value (which in this context would have no useful meaning) but would indicate a very large count, near to its maximum count. This would imply falsely an extremely high degree of contamination of the carrier gas. This situation is avoided by suitable arrangement of the comparator 9. A suitable voltage source 21 is connected to a bank of switches indicated collectively by reference 22. Each of the switches 22 is connected to an input (BO to BN) of comparator 9. The other set of comparator inputs (AO to AN) are connected to respective units of the measuring counter 4. Each switch connected to the comparator 9 is also connected through a resistor to "low" at 23. When any one of the switches 22 is closed, the corresponding comparator input is connected to source 21. When the corresponding unit of counter 4 is activated on a down count the comparator indicates on output 24 that the count in counter 4 is passing below a given number. The output on line 24 is arranged to stop the down count through actuating a gate 25 and a signal on lamp 11 that the test has been passed. The counter 4 can finally be brought to zero by operating the set zero control 19. In FIG. 2, to avoid over-complication, only a few stages of counter 4 and comparator 9 have been shown. Actual zero crossing may be detected through line 26, actuating gate 27. Outputs at 11, 12 actuate green and red signal lamps to indicate whether, as described above, the count reached in measuring counter 4 corresponds to carrier gas flow which has passed or has failed the test for content of contaminant material. Input gates to comparator 9 are provided at 28 and 29, connecting (actual connections not shown) to appropriate A terminals of the counter 4, for setting the count values at which the measuring crystal 1 is usable freely, and usable for one more test respectively. Red, yellow and green signal lamps, 13, 14, 15 are operable, as already described, to indicate an unusable, a border-line, or a usable state of the crystal 1. The blocks indicated by references 30, 31 are concerned with internal switching functions of the apparatus, including latching and the elimination of the effects of contact bounce deriving from mechanical switches. The switches labelled "TEST CRYSTAL" and "RUN TEST" in FIG. 2, being in parallel could functionally be replaced by a single switch. However, from the point of view of logical layout of a control panel for the apparatus, the provision of two switches is preferred.

The crystals 1 and 2 should, for convenience of operation of the apparatus be matched crystals, such that before use in the apparatus they have as nearly as possible identical frequencies of resonance.

I claim:

1. Apparatus for detecting the presence of a contaminant in a gaseous carrier comprising a first piezo electric crystal oscillator (1), a carrier gas feed means (IB) for enabling contaminant to act upon the said first crystal (1) in a manner which changes the effective mass thereof, measuring means (4) for obtaining a first value related to the total number of oscillations of the crystal (1) during a first predetermined period of time, means for enabling the first value to be decreased by a second value related to the total number of oscillations of the crystal (1) during a second time period not greater than said first predetermined time period, testing means (10), said testing means being arranged to allow the first crystal (1) to oscillate for a second predetermined period of time, to obtain a value related to the number of oscillations of the first crystal (1) in said second predetermined period of time, and to compare said value with at least one other preselected value, whereby any change in mass of said crystal (1) due to previous use can be determined by said comparison, and a second piezo electric crystal oscillator (2) the output of which drives a counter (6) to determine the said first predetermined period of time and said second period of time.

2. Apparatus according to claim 1 wherein the means producing said first and second values are counters (4) and (6) each arranged to produce said values as respective numerical counts.

3. Apparatus according to claim 2 further comprising a comparator (9) to compare the numerical count at the end of the said second time period with a numerical count of preset value for providing an indication as to whether the numerical count at the end of the second time period is greater than or less than the preset numerical count.

4. Apparatus according to claim 1 wherein the crystal (2) of the second piezo electrical crystal oscillator is arranged to be exposed to substantially the same environmental conditions affecting its stability as said first crystal, except that shielding means (2A) are provided so that the second crystal (2) is not exposed to contaminant and the mass of said second crystal remains unchanged.

5. Apparatus according to claim 1 further comprising delay means (7) arranged to allow each piezo electric crystal oscillator to oscillate for an initial period of time, and then to switch said oscillator to a respective measuring means.

6. Apparatus according to claim 1 wherein at least the first piezo electric crystal (1) is provided on its surface with a substrate with which contaminant in a gaseous carrier can interact.

7. A method of detecting the presence of a contaminant in a gaseous carrier comprising the steps of allowing a first piezo electric crystal (1) to oscillate for a first predetermined period of time, determining from the oscillations of said first piezo electric crystal during said first predetermined period of time whether there has been any change in mass of said first piezo electric crystal caused by its previous use, allowing the first piezo electric crystal to oscillate for a second predetermined period of time, obtaining a first value proportional to the total number of oscillations by the crystal during the second period of time, allowing contaminant to act upon the crystal (1) in a manner such that the mass of the crystal is changed, allowing the said crystal (1) so acted upon to oscillate for a third time period not greater than said second time period, and decreasing said first value by a second value proportional to the total number of oscillations by the crystal (1) during said third period, said second period of time being defined as that required for a second piezo electrical crystal (2) to effect a predetermined number of oscillations.

8. A method according to claim 7 wherein contaminant acts upon the surface of the said crystal (1) to increase the mass thereof.

9. A method according to claim 7 wherein contaminant interacts with a substrate on the surface of the said crystal (1) to change the mass thereof.

10. A method according to claim 7 wherein the said values are numerical counts.

11. A method according to claim 10 wherein the numerical count at the end of said third period is compared with a preset value to obtain an indication of whether the change in the mass of the said crystal (1) is above or below a particular value represented by the preset value.

12. A method according to claim 7 wherein the second crystal (2) is exposed to substantially the same environmental conditions affecting its stability as the said first crystal (1), except that the second crystal (2) is not exposed to contaminant and the mass of said second crystal remains unchanged.

13. A method according to claim 7 wherein a numerical count is obtained which is related to the change in mass of the crystal (1) due to said previous use, and said numerical count is compared with at least one predetermined numerical count so as to ascertain the extent of the change.

* * * * *